United States Patent [19]

Moll

[11] Patent Number: 5,725,555
[45] Date of Patent: Mar. 10, 1998

[54] ATRAUMATIC NEEDLE FOR SURGICAL SUTURING MACHINES

[76] Inventor: Clemens Moll, Königsbergerstrasse D52076, Aachen, Germany

[21] Appl. No.: 612,851

[22] PCT Filed: Sep. 3, 1994

[86] PCT No.: PCT/EP94/02945

§ 371 Date: Feb. 23, 1996

§ 102(e) Date: Feb. 23, 1996

[87] PCT Pub. No.: WO95/09568

PCT Pub. Date: Apr. 13, 1995

[30] Foreign Application Priority Data

Oct. 1, 1993 [DE] Germany .............. 43 33 545

[51] Int. Cl.$^6$ ........................... A61B 17/06
[52] U.S. Cl. ........................... 606/223; 606/222
[58] Field of Search .............. 606/223, 222–226; 66/116–117; 223/102–104; 289/16; 112/222

[56] References Cited

U.S. PATENT DOCUMENTS

| 2,336,689 | 12/1943 | Karle | 606/223 |
| 5,046,438 | 9/1991 | Hakui | 112/222 |
| 5,178,628 | 1/1993 | Otsuka et al. | 606/223 |
| 5,476,480 | 12/1995 | Matsutani et al. | 606/222 |

FOREIGN PATENT DOCUMENTS

| 37 02 015 A1 | 8/1987 | Germany . |
| 37 12 163 A1 | 10/1988 | Germany . |

*Primary Examiner*—Michael Buiz
*Assistant Examiner*—Tina T. D. Pham
*Attorney, Agent, or Firm*—McGlew and Tuttle

[57] ABSTRACT

An atraumatic needle intended for use in surgical suturing machines has a shaft curved in a defined manner and is provided with a cutting tip located on the outer radius of curvature of the shaft.

10 Claims, 1 Drawing Sheet

ATRAUMATIC NEEDLE FOR SURGICAL SUTURING MACHINES

FIELD OF THE INVENTION

The present invention pertains to an atraumatic needle for use in surgical suturing machines, which has a plunger for receiving the needle in a needle holder moving on an arc-shaped path, as well as an essentially cylindrical and curved shaft with an eye for the passage of the thread, and a tip joining the eye.

BACKGROUND OF THE INVENTION

The preparation of sutures by hand in tissues in human medicine and veterinary medicine requires, on the one hand, a great skill, and, depending on the structure of the tissue, it is possible only by the application of relatively strong forces by the surgeon. Needles with a so-called cutting tip, which have, e.g., the shape of a triangular tip (cf. DE-OS 37 12 163), have been used, among other things, to reduce the piercing force to be applied.

Even though surgical suturing machines, which are described in, e.g., DE-PS 37 02 015, are able to apply the piercing forces occurring during the use of a device provided with a conical tip, a strong force and consequently a relatively high pressure, which lead to deformations of the edge area of the insertion channel (a hole or opening formed by the insertion of the needle in the skin parts), are applied here to the tissue surfaces prior to the insertion proper. Even though such deformations affect only an area of a few tenths of one millimeter, they nevertheless reduce the reliability of suture formation insofar as the thread loop to be grasped by the shuttle of the surgical suturing machine is not sufficient or—relative to the movement of the shuttle—is not in the correct position or it is not formed at the correct point in time during the movement of the shuttle.

Since the formation of so-called missed stitches may lead to serious consequences for the patient, especially in human medicine, it is necessary to ensure, already at the time of insertion of the needle into the tissue, that the insertion forces generated in this process will not unfavorably affect the subsequent stitch formation.

SUMMARY AND OBJECTS OF THE INVENTION

The primary object of the present invention is therefore to provide a needle for surgical suturing machines which does not exert any effect on the tissue that would compromise the reliability of stitch formation and especially of loop formation during its insertion into the tissue, on the one hand, and which does not expand the insertion channel beyond the absolutely necessary extent, on the other hand.

According to the invention, an atraumatic needle is provided for use in surgical suturing machines, which has a plunger for receiving the atraumatic needle and a needle holder moving on an arc-shaped path, as well as an essentially cylindrical and curved shaft with an eye for the passage of the thread, and a tip joining the eye. The radius of curvature of the shaft essentially corresponds to the radius of curvature of its path of movement. A flattened area (flattened surface) is provided in the area of the tip on both the outer surface and the inner surface of the shaft. The two flattened areas extend at acute angles in relation to one another. A cutting line of the flattened area is located on the outer radius of curvature of the shaft to form an edge. The edge is directed at right angles to a longitudinal axis of a shaft and is located essentially on the outer radius of curvature of the shaft.

The invention provides that no deformations occur in the edge area of the insertion channel due to the design according to the present invention, particularly due to the equal radii of curvature of both the shaft and its path of movement. The invention also provides that the lateral forces generated due to and during the formation of the insertion channel are considerably reduced due to the spade-shaped edge arranged on the outer surface of the shaft, and they always act only in one direction, namely, in the direction of the outer surface of the shaft. Deformations in the edge area of the insertion channel are avoided as a result further, the shaft of the needle is always pressed to the outside so that the same frictional forces and also the same friction conditions occur for the formation of the thread loop, and the thread loop is therefore always formed uniformly and can be reliably grasped by the shuttle. The necessary insertion force is further reduced and the edge area of the insertion channel is spared even more as a result of the edge being modified so that the edge is located asymmetrically to the longitudinal axis of the shaft extending through the eye, and is rounded.

A further improvement in the insertion conditions is achieved in that the edge is formed by two arcs with different radii (r1, r2), with centers (M1, M2) located in a plane directed essentially in parallel to the central longitudinal plane of the needle.

A simple adjustment in terms of design of the radius of curvature of the shaft to the radius of curvature of its path of movement can be achieved with an intermediate piece extending at an angle in relation to the shaft. The intermediate piece is provided between the plunger and the shaft of the needle, and the radius of curvature of the shaft is increased as a result.

Especially reliable grasping of the thread loop by the shuttle is achieved if its tip grasping the loop can grasp the thread loop as close to the eye of the needle as possible. To guarantee this, the shaft has a recess for the shuttle on its side facing the shuttle of the suturing machine in the area of the eye.

Reliable guiding of the thread between the guide means of the suturing machine arranged directly in front of the needle and the eye of the needle, as well as a reduction of the frictional forces generated during the insertion of the needle into the tissue between this tissue and the needle are achieved by the shaft having a thread guide on its side located opposite the recess for the shuttle. This thread guide may be formed either by a groove ending in the area of the eye or by a hole opening in the area of the eye.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
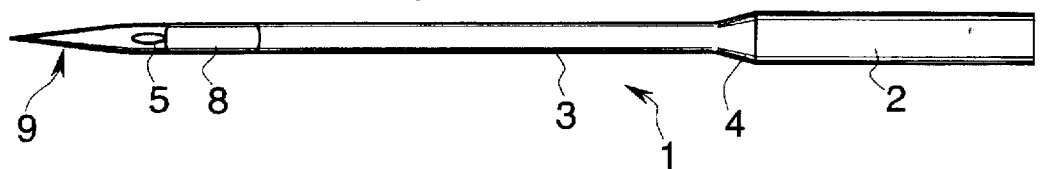
FIG. 1 is a front view of an atraumatic needle on an enlarged scale.

The atraumatic needle, whose front view is shown in FIG. 1, has a plunger 2 of an essentially cylindrical design, which is mounted in a holder of a surgical suturing machine as is shown in, e.g., DE-PS 37 02 015. Corresponding to the kinematic design of such a surgical suturing machine, the needle moves on a circular path of movement.

An intermediate piece 4, which may also have a cylindrical cross section whose diameter is smaller than the diameter of the plunger 2, is arranged between the plunger 2 and the shaft 3 proper of the needle. The intermediate piece 4 extends (see FIG. 2) at a defined angle to both the plunger 2 and the shaft 3, and the transitions from the plunger 2 to the intermediate piece 4 as well as from this to the shaft 3 are rounded. The shaft 3 has an arc-shaped design, and its radius of curvature corresponds to the radius of curvature of its path of movement with the needle inserted into the holder of the suturing machine, so that no relative movements resulting from differences in the radii of curvature of the shaft and the path of movement occur between the needle and the tissue during the penetration of the tip of the needle into the tissue, so that only extremely weak lateral forces are exerted on the tissue at best, and the tissue cannot therefore be damaged in the edge area of the insertion channel.

An eye 5 for receiving or passing through the thread to be used for suturing is provided on the shaft 3 extending at a right angle to a longitudinal direction of the needle in the area of an end of the needle opposite a needle end with the plunger 2. A thread guide 6 is provided on the side of the shaft, which is the top side in FIG. 2, between the transition of the shaft to the intermediate piece 4 and the eye 5. Corresponding to FIG. 3, this thread guide may be formed by a groove 7, whose opening width and depth are adapted to the thickness of the thread to be used for suturing. The groove 7 extends in parallel to the top side of the shaft from the intermediate piece 4 to the eye 5. In another embodiment, not specifically shown, the thread guide may be formed by a hole of a corresponding diameter, which also extends from the intermediate piece 4 to the eye 5 and extends essentially in parallel to the top side of the shaft 3.

Figure 2:
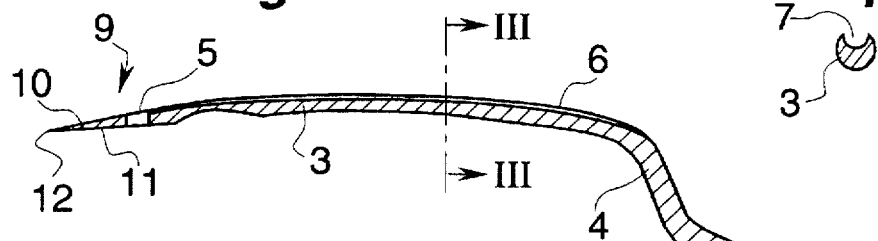
FIG. 2 is a longitudinal sectional view through the needle according to FIG. 1.
Figure 3:
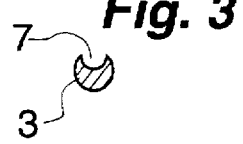
FIG. 3 is a sectional view along line III—III in FIG. 2.
Figure 4:
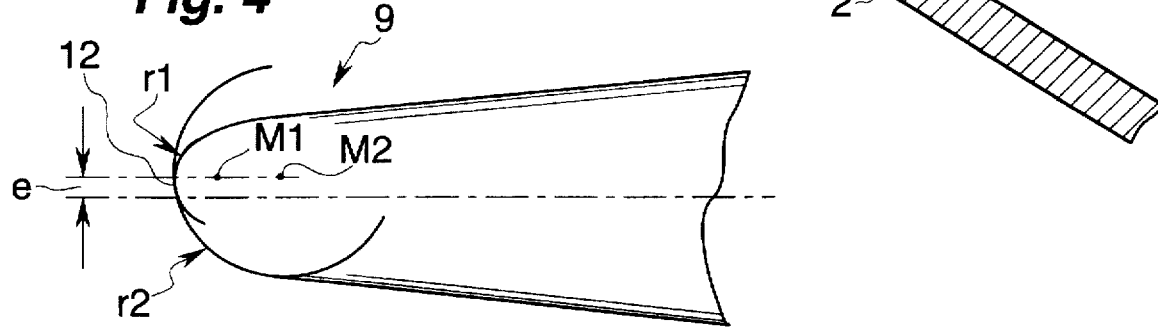
FIG. 4 is a representation of the area of the tip of the needle on a scale even larger than that of FIG. 1.
Figure 5:
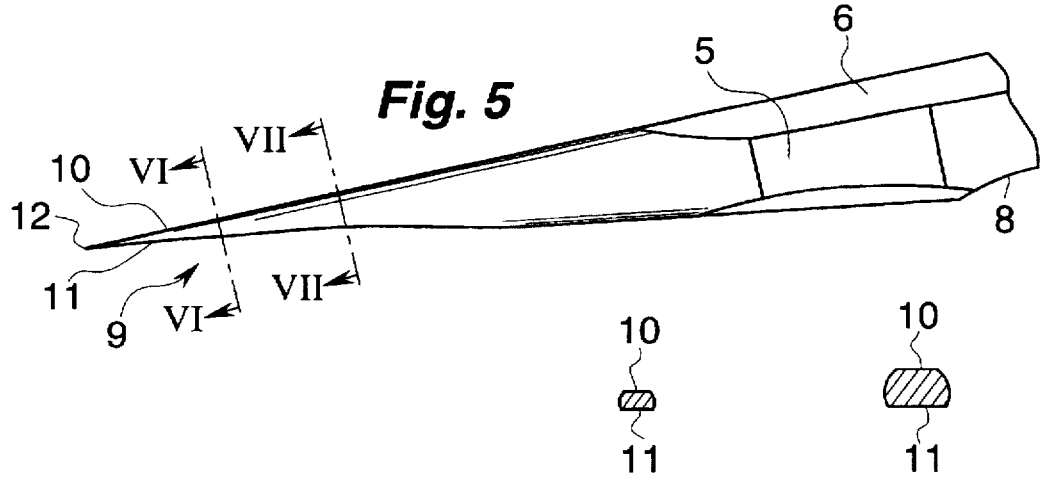
FIG. 5 is a representation of the area of the tip of the needle on a scale larger than that of the longitudinal section according to FIG. 2.
Figures 6, 7:
FIG. 6 is a sectional view along line VI—VI in FIG. 5.
FIG. 7 is a sectional view along line VII—VII in FIG. 5.

On the inner curvature side of the shaft which is the inner or lower side in FIG. 2 and which is on the side of the shaft facing the shuttle with the needle inserted into the holder of the suturing machine, a recess 8 is provided for the shuttle opposite the thread guide 6, and this recess makes possible a short lateral distance between the shaft 3 and the shuttle and consequently reliable grasping of the thread loop.

The tip 9 of the needle joining the eye 5 has a cylindrical or conical cross section, on the outer curvature side of which a flattened area 10 is provided. To form a cutting edge 12 directed essentially at right angles to the longitudinal axis of the needle, a flattened area 11 is also provided on the inner curvature side of the tip 9, and the two flattened areas 10, 11 extend at an acute angle in relation to one another, and their cutting line (line of intersection) lies essentially on the outside of the tip 9. The spade-shaped cutting edge 12 formed hereby consequently lies on the outer radius of curvature of the tip 9 and consequently eccentrically to the central longitudinal axis of the needle or shaft.

In another embodiment of the present invention, not shown, a plurality of flattened areas may be provided instead of the two flattened areas 10, 11, so that a plurality of edges extending at right angles to the needle axis are formed, whose cross-section areas may have the shape of a triangle or another polygon.

In the exemplary embodiment of the present invention shown in the drawing, the two end areas of the cutting edge 12 are rounded, and the rounded areas are formed by two arcs of different radii R1 and R2. The two centers M1 and M2 of the arcs are located laterally to the longitudinal axis of the needle by an amount "e" and consequently in a plane directed essentially in parallel to the central longitudinal plane of the needle, which plane is located at a distance "e" from the central longitudinal plane of the needle. A further reduction in both the insertion forces and the deformations in the edge area of the insertion channel is achieved as a result.

While specific embodiments of the invention have been shown and described in detail to illustrate the application of the principles of the invention, it will be understood that the invention may be embodied otherwise without departing from such principles.

I claim:

1. An atraumatic needle for use in surgical suturing machines, the atraumatic needle comprising:

a plunger for receiving the atraumatic needle in a needle holder, the needle holder being moved on an arc-shaped path; and an essentially cylindrical and curved shaft connected to said plunger, said shaft defining an inner curvature side and an outer curvature side with an eye for the passage of a thread and a tip joining the eye, a radius of curvature of said shaft substantially corresponding to a radius of curvature of said path of movement, said tip having an area with an outer curvature side surface with a flattened region of said shaft and an inner curvature side surface with a flattened region of said shaft, said flattened regions extending at acute angles in relation to one another and defining a cutting line located on an outer radius of curvature of said shaft to form an edge, said edge being directed at a right angle to a longitudinal axis of said shaft and being located essentially on an outer radius of curvature of said shaft.

2. An atraumatic needle according to claim 1, wherein said edge is located asymmetrically with respect to a longitudinal axis of said shaft extending through said eye, said edge being rounded.

3. An atraumatic needle according to claim 2, wherein said edge is formed by two arcs with different radii (r1, r2), based on centers (M1, M2) located in a plane directed essentially parallel to a central longitudinal plane of the atraumatic needle.

4. An atraumatic needle according to claim 1, further comprising: an intermediate piece extending at an angle in relation to said shaft and arranged between said plunger and said shaft, said plunger extending at an angle in relation to said intermediate piece.

5. An atraumatic needle according to claim 1, wherein said shaft has a recess for a shuttle, on a side facing the shuttle in an area of said eye.

6. An atraumatic needle according to claim 5, wherein said shaft has a thread guide on a side located opposite said recess.

7. An atraumatic needle according to claim 6, wherein said thread guide is formed by a groove ending in an area of said eye.

8. An atraumatic needle according to claim 6, wherein said thread guide is formed by a hole opening in an area of said eye.

9. An atraumatic needle for use in surgical suturing machines, the needle being connected to a needle holder moved on an arc-shaped path, the atraumatic needle comprising:

an essentially cylindrical and curved shaft with an eye for the passage of a thread and a tip joining the eye, a radius of curvature of said shaft substantially corresponding to a radius of curvature of said path of movement, said tip having an area with a surface with a flattened region of said shaft and another surface with a flattened region of said shaft, said flattened regions extending at acute angles in relation to one another and defining a cutting line located on an outer radius of curvature of said shaft to form an edge, said edge being directed at a right angle to a longitudinal axis of said shaft and being located essentially on an outer radius of curvature of said shaft;

a plunger for receiving the atraumatic needle in a needle holder;

an intermediate piece extending at an angle in relation to said shaft and arranged between said plunger and said shaft, said plunger extending at an angle in relation to said intermediate piece.

10. An atraumatic needle for use in surgical suturing machines, the needle being connected to a needle holder said plunger being connected to said shaft and moved on an arc-shaped path, the atraumatic needle comprising:

an essentially cylindrical and curved shaft with an eye for the passage of a thread and a tip joining the eye, a radius of curvature of said shaft substantially corresponding to a radius of curvature of said path of movement, said tip having an area with a surface with a flattened region of said shaft and another surface with a flattened region of said shaft, said flattened regions extending at acute angles in relation to one another and defining a cutting line located on an outer radius of curvature of said shaft to form an edge, said edge being directed at a right angle to a longitudinal axis of said shaft and being located essentially on an outer radius of curvature of said shaft; and a plunger connected to said essentially cylindrical and curved shaft, said plunger for receiving the atraumatic needle in a needle holder.

* * * * *